United States Patent
Cao et al.

(10) Patent No.: US 9,061,901 B2
(45) Date of Patent: Jun. 23, 2015

(54) NANONOZZLE DEVICE ARRAYS: THEIR PREPARATION AND USE FOR MACROMOLECULAR ANALYSIS

(75) Inventors: Han Cao, Philadelphia, PA (US); Parikshit A. Deshpande, Princeton, NJ (US); Michael D. Austin, Philadelphia, PA (US); Michael Boyce-Jacino, Titusville, NJ (US)

(73) Assignee: BioNano Genomics, Inc., San Diego, CA (US)

( * ) Notice: Subject to any disclaimer, the term of this patent is extended or adjusted under 35 U.S.C. 154(b) by 749 days.

(21) Appl. No.: 12/374,141

(22) PCT Filed: Jul. 19, 2007

(86) PCT No.: PCT/US2007/016408
§ 371 (c)(1),
(2), (4) Date: Aug. 25, 2009

(87) PCT Pub. No.: WO2008/079169
PCT Pub. Date: Jul. 3, 2008

(65) Prior Publication Data
US 2009/0305273 A1 Dec. 10, 2009

Related U.S. Application Data

(60) Provisional application No. 60/831,772, filed on Jul. 19, 2006, provisional application No. 60/908,582, filed on Mar. 28, 2007, provisional application No. 60/908,584, filed on Mar. 28, 2007.

(51) Int. Cl.
*C12M 1/34* (2006.01)
*C12Q 1/68* (2006.01)
(Continued)

(52) U.S. Cl.
CPC .......... *B82Y 30/00* (2013.01); *B01L 3/502761* (2013.01); *B01L 2200/0663* (2013.01);
(Continued)

(58) Field of Classification Search
CPC ...... C12Q 1/6869; C12Q 1/6816; C12Q 1/68; G01N 21/6428; G01N 21/6486; G01N 33/48721; B01L 3/502761
USPC ......... 435/6.1, 283.1, 287.2, 288.5; 422/68.1, 422/82.05; 536/23.1; 977/701, 704
See application file for complete search history.

(56) References Cited

U.S. PATENT DOCUMENTS 5,427,663 A 6/1995 Austin et al.
5,837,115 A 11/1998 Austin et al.
(Continued)

FOREIGN PATENT DOCUMENTS

CN 1379857 A 11/2002
JP 2003-507026 2/2003
(Continued)

OTHER PUBLICATIONS

Guo et al, Fabrication of Size-Controllable Nanofluidic Channels by Nanoimprinting and Its Application for DNA Stretching, 2004, 4, 69-73.*
(Continued)

*Primary Examiner* — Narayan Bhat
(74) *Attorney, Agent, or Firm* — Knobbe Martens Olson & Bear LLP

(57) ABSTRACT

Constricted nanochannel devices suitable for use in analysis of macromolecular structure, including DNA sequencing, are disclosed. Also disclosed are methods for fabricating such devices and for analyzing macromolecules using such devices.

31 Claims, 9 Drawing Sheets

(51) Int. Cl.

| | | |
|---|---|---|
| *G01N 15/06* | (2006.01) | |
| *G01N 21/00* | (2006.01) | |
| *C07H 21/02* | (2006.01) | |
| *B82Y 30/00* | (2011.01) | |
| *B01L 3/00* | (2006.01) | |
| *G01N 33/487* | (2006.01) | |
| *G01N 35/10* | (2006.01) | |

(52) U.S. Cl.
CPC ...... *B01L2200/12* (2013.01); *B01L 2300/0645* (2013.01); *B01L 2300/0816* (2013.01); *B01L 2300/0822* (2013.01); *B01L 2300/0896* (2013.01); *B01L 2400/0415* (2013.01); *B01L 2400/0487* (2013.01); *C12Q 1/6869* (2013.01); *G01N 33/48721* (2013.01); *G01N 2035/1039* (2013.01)

(56) References Cited

U.S. PATENT DOCUMENTS

| | | | |
|---|---|---|---|
| 5,867,266 | A | 2/1999 | Craighead |
| 6,210,896 | B1 | 4/2001 | Chan et al. |
| 6,214,246 | B1 | 4/2001 | Craighead |
| 6,263,286 | B1 | 7/2001 | Gilmanshin et al. |
| 6,344,319 | B1 | 2/2002 | Bensimon et al. |
| 6,355,420 | B1 | 3/2002 | Chan |
| 6,403,311 | B1 | 6/2002 | Chan |
| 6,438,279 | B1 | 8/2002 | Craighead et al. |
| 6,464,842 | B1 | 10/2002 | Golovchenko et al. |
| 6,627,067 | B1 | 9/2003 | Branton et al. |
| 6,635,163 | B1* | 10/2003 | Han et al. ............ 204/450 |
| 6,696,022 | B1 | 2/2004 | Chan et al. |
| 6,753,200 | B2 | 6/2004 | Craighead et al. |
| 6,762,059 | B2 | 7/2004 | Chan et al. |
| 6,772,070 | B2 | 8/2004 | Gilmanshin et al. |
| 6,790,671 | B1 | 9/2004 | Austin |
| 6,927,065 | B2 | 8/2005 | Chan et al. |
| 7,217,562 | B2 | 5/2007 | Cao et al. |
| 7,262,859 | B2 | 8/2007 | Larson et al. |
| 7,282,330 | B2 | 10/2007 | Zhao et al. |
| 7,316,769 | B2 | 1/2008 | Craighead et al. |
| 7,351,538 | B2 | 4/2008 | Fuchs et al. |
| 7,371,520 | B2 | 5/2008 | Zhao et al. |
| 7,402,422 | B2 | 7/2008 | Fuchs et al. |
| 7,427,343 | B2 | 9/2008 | Han et al. |
| 7,833,398 | B2 | 11/2010 | Craighead et al. |
| 7,918,979 | B2 | 4/2011 | Han et al. |
| 7,960,105 | B2 | 6/2011 | Schwartz et al. |
| 8,168,380 | B2 | 5/2012 | Chan et al. |
| 2002/0110818 | A1 | 8/2002 | Chan |
| 2002/0119455 | A1 | 8/2002 | Chan |
| 2002/0123063 | A1 | 9/2002 | Gjerde et al. |
| 2003/0066749 | A1 | 4/2003 | Golovchenko et al. |
| 2003/0104428 | A1 | 6/2003 | Branton et al. |
| 2003/0235854 | A1 | 12/2003 | Chan et al. |
| 2004/0009612 | A1 | 1/2004 | Zhao et al. |
| 2004/0033515 | A1 | 2/2004 | Cao et al. |
| 2004/0166025 | A1 | 8/2004 | Chan |
| 2004/0197843 | A1 | 10/2004 | Chou et al. |
| 2005/0082204 | A1* | 4/2005 | Schwartz et al. ............. 209/1 |
| 2006/0011862 | A1 | 1/2006 | Bernstein |
| 2006/0275911 | A1 | 12/2006 | Wang |
| 2007/0128083 | A1 | 6/2007 | Yantz |
| 2007/0161028 | A1 | 7/2007 | Schwartz et al. |
| 2008/0003689 | A1 | 1/2008 | Lee |
| 2008/0085552 | A1 | 4/2008 | Larson et al. |
| 2008/0103296 | A1 | 5/2008 | Zhao |
| 2008/0254549 | A1 | 10/2008 | Fuchs |
| 2011/0210272 | A1 | 9/2011 | Chan et al. |
| 2012/0196382 | A1 | 8/2012 | Chan et al. |
| 2012/0217161 | A1 | 8/2012 | Chan et al. |

FOREIGN PATENT DOCUMENTS

| | | |
|---|---|---|
| JP | 2005-533636 | 11/2005 |
| WO | WO 98/35012 A | 8/1998 |
| WO | WO 00/79257 | 12/2000 |
| WO | WO 01/13088 | 2/2001 |
| WO | WO 01/13088 A | 2/2001 |
| WO | WO0113088 A1 | 2/2001 |
| WO | WO02/099398 | 12/2002 |
| WO | WO 03/106693 | 12/2003 |
| WO | WO2005078137 | 8/2005 |

OTHER PUBLICATIONS

Nath et al, A System for Micro/Nano Fluidic Flow Diagnostics, 2005, Biomedical Microdevices, 7, 169-177.*
Hashioka, et al. "Simple and Quick Detection of Target DNA by Hybridization in Nano Gap Channel Array." 9th International Conference on Miniaturized Systems for Chemistry and Life Sciences, vol. 1, pp. 730-732 (2005).
Japanese Office Action dated Jul. 24, 2012 for Japanese Patent Application No. 2009-520847 filed Jul. 19, 2007 (English translation thereof is enclosed).
Mannion et al., Conformational Analysis of Single DNA Molecule Undergoing Entropically Induced Motion in Nanochannels, Biophysical Journal, Jun. 2006, vol. 90, pp. 4538-4545.
Office Action dated May 9, 2012 for Australian Patent Application No. 2007338862, filed Jul. 19, 2007.
Notice of Allowance dated Jan. 23, 2014 for Australian Patent Application No. 2007338862, filed Jul. 19, 2007.
Office Action dated Mar. 28, 2013 for Canadian Patent Application No. 2658122, filed Jul. 19, 2007.
Notice of Allowance dated Dec. 11, 2013 for Canadian Patent Application No. 2658122, filed Jul. 19, 2007.
Office Action dated Jan. 4, 2012 for Chinese Patent Application No. 200780034694.9 filed Jul. 19, 2007.
Office Action dated Nov. 5, 2012 for Chinese Patent Application No. 200780034694.9 filed Jul. 19, 2007.
Office Action dated Feb. 5, 2013 for Japanese Patent Application No. 2009-520847 filed Jul. 19, 2007.
Office Action dated Dec. 9, 2013 for Japanese Patent Application No. 2009-520847 filed Jul. 19, 2007.
International Preliminary Report on Patentability dated Feb. 23, 2009 for International Patent Application No. PCT/US2007/016408 filed Jul. 19, 2007.
Office Action dated Mar. 25, 2014 in Chinese Patent Application No. 201310054745.1 filed Feb. 20, 2013.
Slater, et al., "Bidirectional Transport of Polyelectrolytes Using Self-Modulating Entropic Ratchets," Physical Review Letters, The American Physical Society, 78(6), Feb. 1997, 1170-1173.
The Quest for the $1,000 Human Genome, by Nicholas Wade, *The New York Times*, Jul. 18, 2006.
"Spanning the Drug Pipeline," Tanuja Koppel, PhD Senior Editor, Drug Discovery & Development, Sep. 13, 2005, 1 page, http://www.dddmag.com.
"Small-Animal Models Advance in Vivo ADME-Tox," Patrick McGee, Senior Editor, Drug Discovery & Development, Jul. 5, 2005, 3 pages, http://www.dddmag.com.
"New In Vitro, Modeling Tools May Cut Tox Attrition," Patrick McGee, Senior Editor, Drug Discovery & Development, Aug. 4, 2005, 4 pages, http://www.dddmag.com.
Austin RH, Tegenfeldt JO, Cao H, Chou SY, Cox EC, (2002) "Scanning the Controls: Genomics and Nanotechnogloy," IEEE Transactions on Nanotechnology 1: 12-18.
Cai W, Aburatani H, et al. (1995) "Ordered restriction endonuclease maps of artificial chromosomes created by optical mapping on surfaces," PNAS 92: 5164-8.
Cao H, Tegenfeldt JO, Austin RH, Chou SY, (2002) "Gradient nanostructures for interfacing microfluidics and nanofluidics," Applied Physics Letters 81: 3058-3060.
Cao, H. et al., "Fabrication of 10 nm enclosed nanofluidic channels," Applied Physics Letters, AIP, American Institute of Physics, Melville, NY, 18(1), Jul. 2002, 174-176.

(56) References Cited

OTHER PUBLICATIONS

Chan EY, Goncalves NM, et al. (2004) "DNA mapping using microfluidic stretching and single molecule detection of fluorescent site-specific tags," Genome Research 14: 1137-1146.
Chang H, Kosari F, Andreadakis G, Alam MA, Vasmatzis G, Bashir R, (2004) "DNA-Mediated Fluctuations in Ionic Current through Silicon Oxide Nanopore Channels," Nano Letters 4: 1551-1556.
Chen P, Gu J, Brandin E, KYR, Wang Q, Branton D, (2004) "Probing Single DNA Molecule Transport Using Fabricated Nanopores," Nano Letters 4: 2293-2298.
Chen P, Mitsui T, Farmer DB, Golovchenko J, Gordon RG, Branton D, (2004) "Atomic Layer Deposition to Fine-Tune the surface Properties and Diameters of Fabricated Nanopores," Nano Letters 4: 1333-1337.
Conrad DF et al., (2006) "A high-resolution survey of deletion polymorphism in the human genome," Nature Genetics 38: 75-81.
Deamer DW, Branton D, (2002) "Characterization of Nucleic Acids by Nanopore Analysis," Acc Chem Res 35: 817-825.
Deegan R, Bakajin O, et al. "Contact line deposits in an evaporating drop," Physical Review E, Jul. 2000, 62(1), 756-765.
Delphine Purves et al, "Genotoxicity testing: Current Practices and Strategies Used by the Pharmaceutical Industry," *Mutagenesis*, 1995, vol. 10 No. 4 pp. 297-312.
Dietrich, et al., "Advances in the Development of a Novel Method to be used in Proteomics using Gold Nanobeads," *Ultrasensitive and Single-Molecule Detection Technologies*, edited by Jorg Enderlein, et al, Proc. of SPIE vol. 6092, 6092C (2006).
Eichler EE, (2006) "Widening the spectrum of human genetic variation," Nature Genetics 38: 9-11.
FDA Redbook 2000 Genotoxicity Tests, available at www.cfsan.fda.gov.
Gad S, Aurias A, et al. (2001). "Color bar coding the BRCA1 gene on combed DNA: A useful strategy for detecting large gene arrangements." Genes, Chromosomes and Cancer 31: 75-84.
Gad S, Klinger M, et al. (2002). "Bar code screening on combed DNA for large rearragements of the BRCA1 and BRCA2 genes in French breast cancer families." J Med Genet 39: 817-21.
Gracheva ME, Xiong A, Aksimentiev A, Schulten K, Timp G, Leburton JP, (2006) "Simulation of the electric response of DNA translocation through a semiconductor nanopore-capacitor," Nanotechnology 17: 622-633.
Guidance for industry S2B Genotoxicity: A standard Battery for Genotoxicity Testing of Pharmaceuticals, Jul. 1997, ICH.
Henriquez, R.R. et al., "The resurgence of Coulter counting for analyzing nanoscale objects," The Analyst, 2004, 129, 478-482.
Hinds DA et al., (2006) "Common deletions and SNPs are in linkage disequilibrium in the human genome," Nature Genetics 38: 82-85.
Howorka S, Cheley S, Bayley H, (2001) "Sequence-specific detection of individual DNA strands using engineered nanopores," Nature Biotechnology 19: 636-639.
Howorka S, Movileanu L, Braha O, Bayley H, (2001) "Kinetics of duplex formation for individual DNA strands within a single protein nanopore," PNAS 98: 12996-13001.
Johansson B, Mertens F, Mitelman F (1996). "Primary vs. secondary neoplasia-associated chromosomal abnormalities-balanced rearrangements vs genomic imbalances?" Genes, Chromosomes and Cancer 16: 155-163.

Kasianowicz JJ, Brandin E, Branton D, Deamer DW, (1996) "Characterization of individual polynucleotide molecules using a membrane channel," PNAS 93: 13770-13773.
Li J, Gershow M, Stein D, Brandin E, Golovchenko JA, (2003) "DNA molecules and configurations in a solid-state nanopore microscope," Nature Materials 2: 611-615.
Li J, Stein D, MuMullan C, Branton D, Aziz MJ, Golovchenko JA, (2001) "Ion-beam sculpting at nanometer length scales," Nature 412: 166-169.
McCarroll SA et al., (2006) "Common deletion polymorphisms in the human genome," Nature Genetics 38: 86-92.
Meller A, Nivon L, Brandin E, Golovchenko J, Branton D, (2000) "Rapid nanopore discrimination between single polynucleotide molecules," PNAS 97: 1079-1084.
Meller A, Nivon L, Branton D, (2001) "Voltage-Driven DNA Translocations through a Nanopore," Physical Review Letters 86: 3435-3438.
Meng X, Benson K, et al. (1995). "Optical mapping of lambda bacteriophage clones using restriction endonucleases," Nat Genet 9: 432-438.
Mijatovic, D. et al., "Technologies for nanofluidic systems: top-down vs. bottom-up—a review," Lab on a Chip, Royal Society of Chemistry, Cambridge, GB, Jan. 2005, vol. 5, 492-500.
Molecular Devices website, product page for Axopatch 200B: http://www.moleculardevices.com/pages/instruments/cn_axopatch200b.html.
Nagata S, Nagase H, Kawane K, N Mukae, Fukuyama H, (2003) "Degradation of chromosomal DNA during Apoptosis," Cell Death and Differentiation 10: 108-116.
Reccius, C.H. et al., "Compression and Free Expansion of Single DNA Molecules in Nanochannels," Phys. Rev. Letts., Dec. 21, 2005, 95, 268101-1-268101-4.
Storm AJ, Chen JH, Ling XS, Zandbergen HW, Dekker C, (2003) "Fabrication of solid-state nanopores with single-nanometer precision," Nature Materials 2: 537-540.
Storm AJ, Storm C, Chen J, Zandbergen H, Joanny JF, Dekker C, (2005) "Fast DNA Translocation through a Solid-State Nanopore," Nano Letters 5: 1193-1197.
Tegenfeldt JO, Prinz C, Cao H, Chou SY, Reisner WW, Riehn R, Wang YM, Cox EC, Sturm JC, Silberzan P, Austin RH, (2004b) "The dynamics of genomic-length DNA molecules in 100-nm channels," PNAS 101: 10979-10983.
Tegenfeldt JO, Prinz C, Cao H, Huang RL, Austin RA, Chou SY, Cox EC, Sturm JC, (2004) "Micro and nanofluidics for DNA analysis," Anal Bioanal Chem 378: 1678-1692.
Wong PK, Lee YK, Ho CM (2003). "Deformation of DNA molecules by hydrodynamic focusing," J Fluid Mechanics 497: 55-65.
Technology Research News, LLC, "Melted fibers make nano channels," Jan. 14, 2004, Retrieved from the internet at URL <http://www.trnmag.com/Stories/2004/011404/Melted_fibers_make_nano_channels_Brief.
Wanli Li, et al., "Sacrificial polymers for nanofluidic channels in biological applications," Nanotechnology, 2003, 14, 578-583.
Hou-Pu Chou et al., "A Microfabricated Device for Sizing and Sorting DNA Molecules," Proc. Natl. Acad. Sci. USA, Jan. 1999, 96, 11-13.
Czaplewski, D.A. et al., "Nanofluidic channels with elliptical cross sections formed using a nonlithographic process," Applied Physics Letters, Dec. 8, 2003, 83(23), 4836-4838.

\* cited by examiner

NANONOZZLE DEVICE ARRAYS: THEIR PREPARATION AND USE FOR MACROMOLECULAR ANALYSIS

CROSS-REFERENCE TO RELATED APPLICATIONS

This application is the National Stage of International Application No. PCT/US2007/016408, filed Jul. 19, 2007, which claims the benefit of U.S. Provisional Application No. 60/831,772, filed Jul. 19, 2006, U.S. Provisional Application No. 60/908,582, filed Mar. 28, 2007, and U.S. Provisional Application No. 60/908,584, filed Mar. 28, 2007, the disclosures of which are incorporated herein by reference in their entireties.

FIELD OF THE INVENTION

The present invention pertains to the field of nanoscale devices. The present invention also pertains to the field of macromolecular sequencing, particularly the field of DNA sequencing and characterization.

BACKGROUND OF THE INVENTION

Various scientific and patent publications are referred to herein. Each is incorporated by reference in its entirety.

Biomolecules such as DNA or RNA are long molecules composed of nucleotides, the sequence of which is directly related to the genomic and post-genomic gene expression information of an organism. In most cases, the mutation or rearrangement of the nucleotide sequences during an individual's life span can lead to disease states such as genetic abnormalities or cell malignancy. In other cases, the small amount of sequence differences among each individual reflects the diversity of the genetic makeup of the population. Because of these differences in genetic sequence, certain individuals respond differently to environmental stimuli and signals, including drug treatments. For example, some patients experience positive response to certain compounds while others experience no effects or even adverse side effects.

The fields of population genomics, medical genomics and pharmacogenomics studying genetic diversity and medical pharmacological implications require extensive sequencing coverage and large sample numbers. The sequencing knowledge generated would be especially valuable for the health care and pharmaceutical industry. Cancer genomics and diagnostics study genomic instability events leading to tumorigenesis. All these fields would benefit from technologies enabling fast determination of the linear sequence of biopolymer molecules such as nucleic acids, or epigenetic biomarkers such as methylation patterns along the biopolymers. There is a long felt need to use very little amount of sample, even as little as a single cell. This would greatly advance the ability to monitor the cellular state and understand the genesis and progress of diseases such as the malignant stage of a cancer cell.

Most genome or epigenome analysis technologies remain too expensive for general analysis of large genomic regions for a large population. In order to achieve the goal of reducing the genomic analysis cost by at least four orders of magnitude, the so-called "$1000 genome" milestone, new technologies for molecular analysis methods are needed. See "The Quest for the $1,000 Human Genome," by Nicholas Wade, The New York Times, Jul. 18, 2006.

One technology developed for fast sequencing involves the use of a nanoscale pore through which DNA is threaded. Historically, the "nanopore" concept used a biological molecular device to produce ionic current signatures when RNA and DNA strands are driven through the pore by an applied voltage. Biological systems, however, are sensitive to pH, temperature and electric fields. Further, biological molecules are not readily integrated with the semiconductor processes required for sensitive on-chip electronics.

Many efforts have been since focused on designing and fabricating artificial nanopores in solid state materials. These methods, however, which are capable of producing only pores in membranes are not capable of producing longer channels needed to achieve true single-molecule sequencing of long biological polymers such as DNA or RNA.

Accordingly, there is a need in the field for devices capable of yielding sequence and other information for long biological polymers such as DNA or RNA.

SUMMARY OF THE INVENTION

In meeting the described challenges, in a first aspect the present invention provides methods for characterizing one or more features of a macromolecule, comprising linearizing a macromolecule residing at least in part within a nanochannel, at least a portion of the nanochannel being capable of physically constraining at least a portion of the macromolecule so as to maintain in linear form that portion of the macromolecule, and the nanochannel comprising at least one constriction; transporting at least a portion of the macromolecule within at least a portion of the nanochannel such that at least a portion of the macromolecule passes through the constriction; monitoring at least one signal arising in connection with the macromolecule passing through the constriction; and correlating the at least one signal to one or more features of the macromolecule.

In a second aspect, the present invention provides devices for analyzing a linearized macromolecule, comprising two or more fluid reservoirs; and a nanochannel comprising a constriction, the nanochannel placing the at least two fluid reservoirs in fluid communication with one another.

Further provided are methods for transporting a macromolecule, comprising providing at least two fluid reservoirs; providing an at least partially linearized macromolecule, at least a portion of the macromolecule residing in a nanochannel, the nanochannel placing the at least two reservoirs in fluid communication with one another, the nanochannel comprising a constriction; and applying a gradient to the macromolecule, the gradient giving rise to at least a portion of the linearized macromolecule being transported within at least a portion of the nanochannel.

Additionally provided are methods for fabricating a constricted nanochannel, comprising providing a nanochannel; the nanochannel having an internal diameter in the range of from about 0.5 nm to about 1000 nm, and the nanochannel having a length of at least about 10 nm; reducing the internal diameter of the nanochannel either at a location within the nanochannel, at a location proximate to the end of the nanochannel, or both, so as to give rise to a constriction within or adjacent to the nanochannel, the constriction having an internal diameter in fluidic communication with the nanochannel, the nanochannel being capable of maintaining a linearized macromolecule in its linearized form, and the reduced internal diameter being capable of permitting the passage of at least a portion of a linearized macromolecule.

Also disclosed are methods for linearizing a macromolecule, comprising placing a macromolecule in a nanochannel, at least a portion of the nanochannel being capable of physically constraining at least a portion of the macromolecule so as to maintain in linear form that portion of the macromolecule.

The general description and the following detailed description are exemplary and explanatory only and are not restrictive of the invention, as defined in the appended claims. Other aspects of the present invention will be apparent to those skilled in the art in view of the detailed description of the invention as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

(FIG. 7b) self-terminating opening of the constriction using an acid etchant terminated by exposure to a neutralizing strong base; and (FIG. 7c) the final nanonozzle device after the etchant and neutralizer are removed;

(FIG. 8a) a sacrificial macromolecule is placed into the nanochannel and allowed to partially exit into the reservoir; (FIG. 8b) the fluid is removed and material is deposited around the sacrificial molecule; and (FIG. 8c) the sacrificial molecule is removed leaving a constriction at the end of the nanochannel; (FIG. 9a) additive deposition of silicon oxide on an open nanochannel of initial width and height of about 150 nm leads to an enclosed nanochannel of about 50 nm diameter, (FIG. 9b) variation of the deposition of parameters leads to smaller enclosed channels, and (FIG. 9c) by extension, a sub-10 nm opening can be created.

DETAILED DESCRIPTION OF ILLUSTRATIVE EMBODIMENTS

Terms

Figure 1:
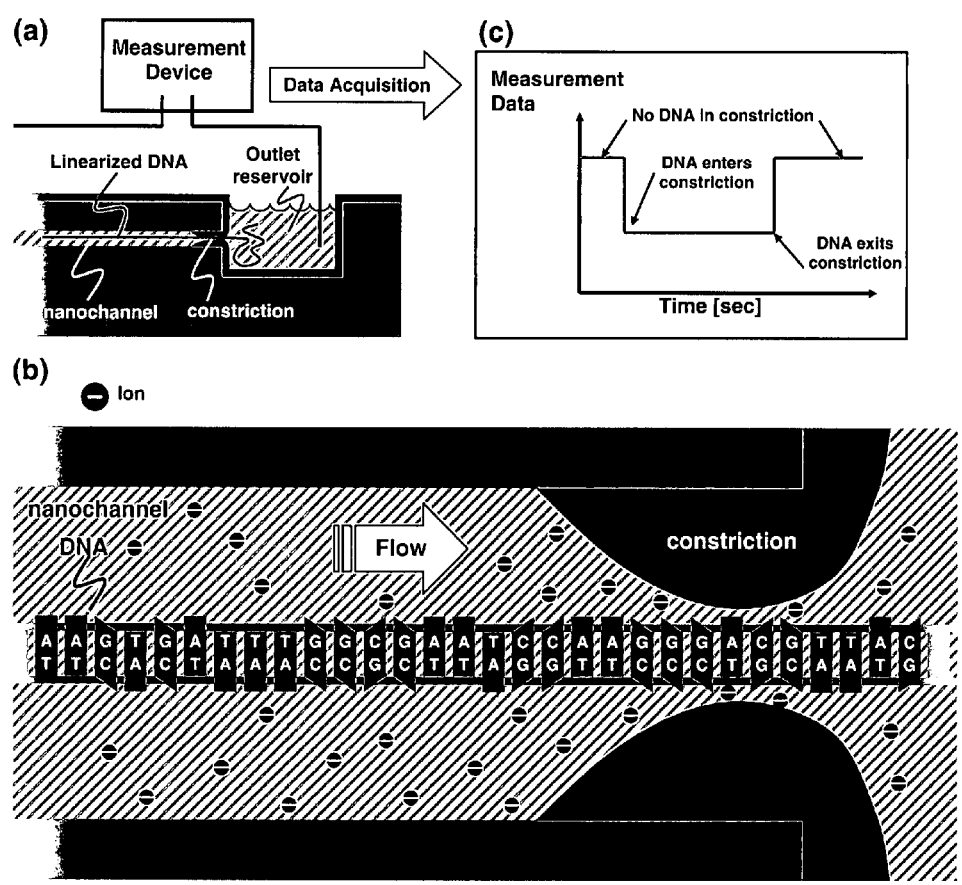
FIG. 1a is a schematic view of a DNA sequencer showing linearized double-stranded DNA passing through a nanochannel into an outlet reservoir, where a measurement device detects physical, chemical, electrical, or other changes in the outlet reservoir or within the nanochannel related to the passage of the DNA.
FIG. 1b depicts a DNA molecule flowing through a nanonozzle constriction at the end of a nanochannel, wherein the DNA molecule is a double-stranded DNA having a first strand comprising a nucleic acid sequence of SEQ ID NO: 1 and a complementary strand comprising nucleic acid sequence of SEQ ID NO: 2.
FIG. 1c depicts the data evolved from the passage of the DNA through the constricted nanochannel.

As used herein, the term "substantially linear" means that the conformation of at least a portion of a long molecule, such as, but not limited to, a polynucleic acid comprising 200 nucleic acids linked together, does not loop back on itself or does not containing any sharp bends or curves greater than about 360 degrees.

As used herein, the term "nanochannel" means a conduit, channel, pipe, duct, or other similar structure having at least one nanoscale dimension.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

In one aspect, the present invention provides methods for characterizing one or more features of a macromolecule. These methods include linearizing a macromolecule residing at least in part within a nanochannel, at least a portion of the nanochannel being capable of physically constraining at least a portion of the macromolecule so as to maintain in linear form that portion of the macromolecule.

Suitable nanochannels have a diameter of less than about twice the radius of gyration of the macromolecule in its extended form. A nanochannel of such dimension is known to begin to exert entropic confinement of the freely extended, fluctuating macromolecule coils so as to extend and elongate the coils. Suitable nanochannels can be prepared according to the methods described in Nanochannel Arrays And Their Preparation And Use For High-Throughput Macromolecular Analysis, U.S. patent application Ser. No. 10/484,293, filed Jan. 20, 2004, the entirety of which is incorporated by reference herein.

Suitable nanochannels include at least one constriction. Such constrictions function to locally reduce the effective inner diameter of the nanochannel. Constrictions can be sized so as to permit the passage of linearized macromolecules.

The methods also include the step of transporting at least a portion of the macromolecule within at least a portion of the nanochannel such that at least a portion of the macromolecule passes through the constriction. This is shown in, for example, FIGS. 1b, 2b, and 3b, in which DNA is shown passing through a nanochannel constriction. Constrictions can be made, for example by depositing material at the end of a nanochannel to seal off the nanochannel, and then etching away a portion of the deposited material until a pore much narrower than the nanochannel is produced. This is further illustrated in FIGS. 6 to 9.

Where a comparatively long macromolecule is to be analyzed, the end of the macromolecule is delivered into one end of the nanochannel. This is accomplished by, for example, gradient structures, that assist such delivery into a nanochannel; suitable gradient structures are described in U.S. Pat. No. 7,217,562, to Cao, et al.

Figure 2:
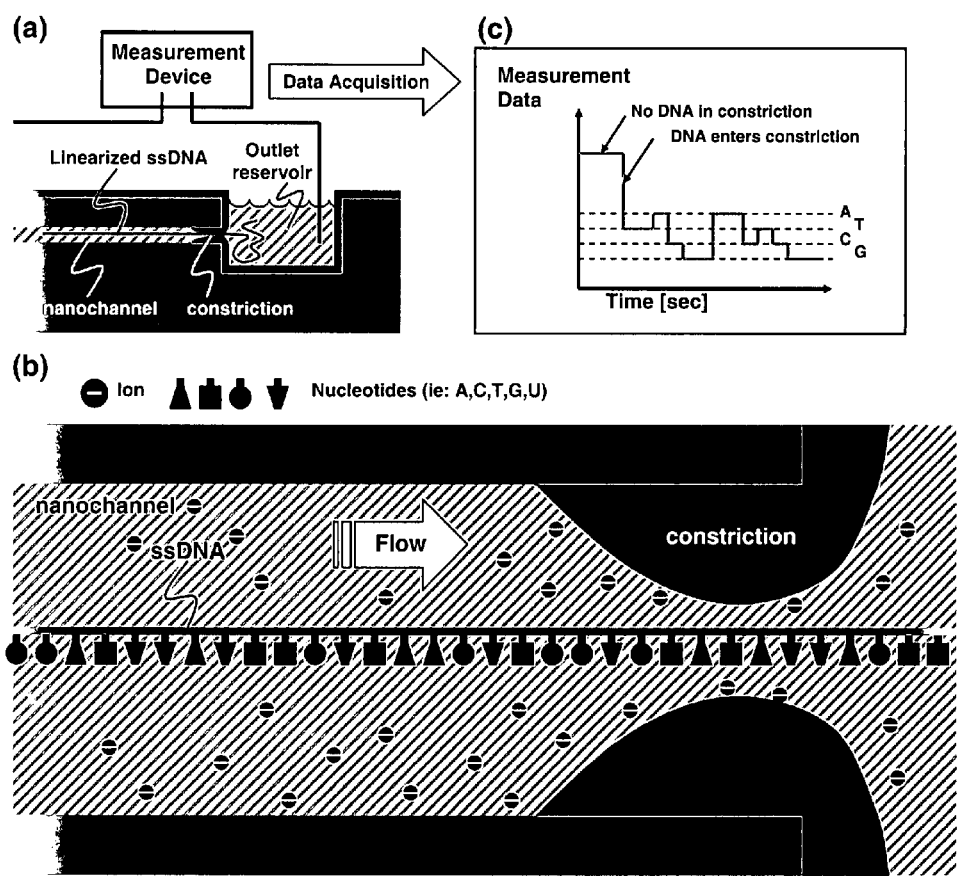
FIG. 2a is a schematic view of a DNA sequencer showing linearized single-stranded DNA passing through a nanochannel into an outlet reservoir, where a measurement device detects any physical, chemical, electrical, or other changes in the outlet reservoir or within the nanochannel related to the passage of the DNA.
FIG. 2b depicts single-stranded DNA molecule flowing through a nanonozzle constriction at the end of a nanochannel.
FIG. 2c depicts the data evolved as individual nucleotides of the single-stranded DNA pass through the constriction of the nanochannel.
Figure 3:
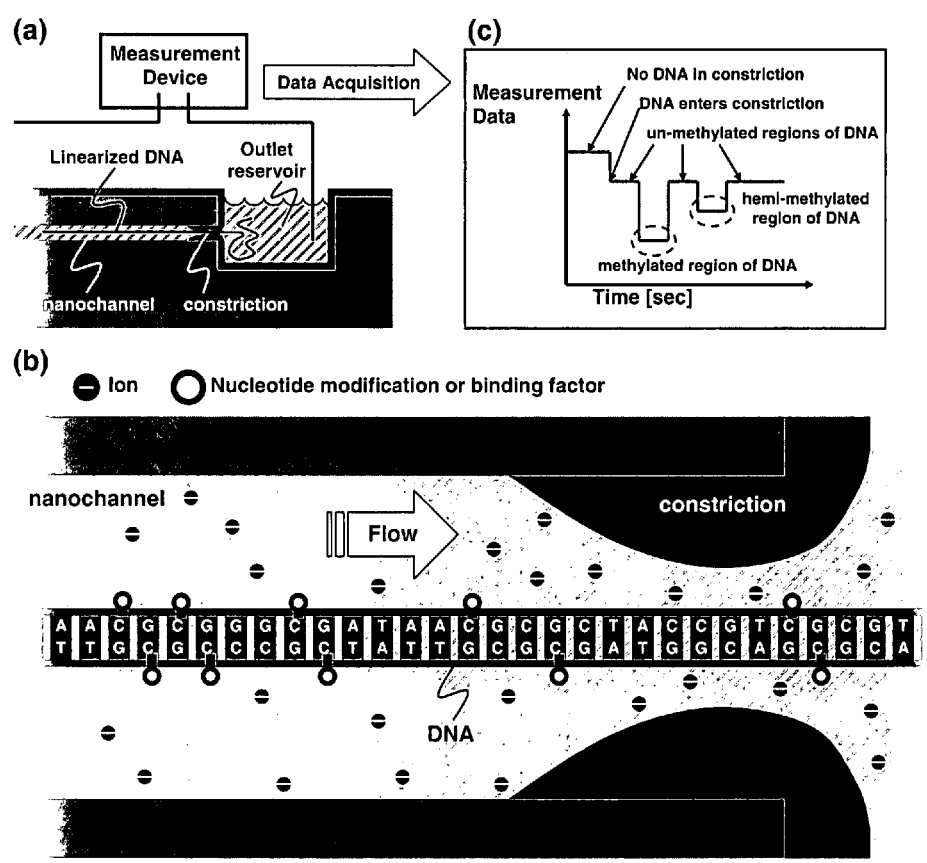
FIG. 3a is a schematic view of a DNA sequencer showing linearized, methylated double-stranded DNA passing through a nanochannel into an outlet reservoir, where a measurement device detects any physical, chemical, electrical, or other changes in the outlet reservoir or within the nanochannel related to the passage of the DNA.
FIG. 3b depicts the methylated double-stranded DNA molecule flowing through a nanonozzle constriction at the end of a nanochannel, wherein the methylated double-stranded DNA molecule is a double-stranded DNA having a first strand comprising a nucleic acid sequence of SEQ ID NO: 3 and a complementary strand comprising a nucleic acid sequence of SEQ ID NO: 4.
FIG. 3c depicts the data evolved as individual nucleotides of the methylated double-stranded DNA pass through the constriction of the nanochannel.

The methods also include monitoring at least one signal arising in connection with the macromolecule passing through the constriction; and correlating the at least one signal to one or more features of the macromolecule. This is depicted in FIGS. 1a, 2a, and 3a, which depict a schematic of monitoring a signal arising in connection with the passage of a macromolecule through a constriction in a nanochannel. Suitable signals include, for example, electric charge signals, optical signals, electromagnetic signals, magnetic signals, or any combination thereof. Electrical signals can be monitored using, for example, any of a variety of commercially available current meters and amplifiers. For example, suitable signal monitoring equipment is capable of applying a constant voltage in the range of from about a nanovolt, or a microvolt, or a millivolt, or even a volt or more across electrodes in contact with liquid within the reservoirs and nanochannel segment. Suitable monitoring equipment is also capable of measuring current between the electrodes many times per second. Suitable equipment will have a bandwidth of at least about 100 Hertz ("Hz", cycles per second), or about 1 kilohertz ("kHz"), or about 10 kHz, or about 100 kHz, or about 1 megahertz ("MHz"), or even about 10 megahertz. Accordingly, current can be made once measurements are variations on the order of the nanosecond, or the microsecond, or even on the millisecond scale. Current amplitude can be from pico seconds . . . . Translocation speed of a sDNA can be around 40 bases per microsecond through a typical "patch clamp amplifier". Best machine today can sample once every microseconds. Axopatch 200B, Molecular Devices (www.moleculardevices.com), having a bandwidth of 100 KHz, is capable of 100,000 current measurements per second, or equivalent to 10 microseconds per current measurement of a change in the current between the electrodes connected to the two waste reservoirs.

Macromolecules suitable for the present method include polynucleotides, polynucleosides, natural and synthetic polymers, natural and synthetic copolymers, dendrimers, surfactants, lipids, natural and synthetic carbohydrates, natural and synthetic polypeptides, natural and synthetic proteins, or any combination thereof. DNA is considered a particularly suitable macromolecule that can be analyzed according to the methods as discussed elsewhere herein.

A macromolecule analyzed according to the methods as provided herein typically resides within a fluid. Suitable fluids include water, buffers, cell media, and the like. Suitable fluids can also be electrolytic, acidic, or basic.

Transporting the macromolecule is accomplished by exposing the macromolecule to a gradient, the gradient suitably applied along the flow direction of a suitable nanochannel. Suitable gradients include an electroosmotic field, an electrophoretic field, capillary flow, a magnetic field, an electric field, a radioactive field, a mechanical force, an electroosmotic force, an electrophoretic force, an electrokinetic force, a temperature gradient, a pressure gradient, a surface property gradient, a gradient of hydrophobicity, a capillary flow, or any combination thereof. An electric field is a particularly suitable gradient.

The gradient may be temporally constant, spatially constant, or any combination thereof. The gradient may also vary in space and time as needed. In some embodiments, varying the gradient enables the transportation of the macromolecule in both forward and reverse directions. In some embodiments, varying the gradient permits the same portion of the macromolecule to be passed through the constriction multiple times.

Varying the gradient also enables the user to advance the macromolecule quickly through the constriction until a region of particular interest on the macromolecule is reached, in a manner analogous to fast-forwarding a cassette tape to a desired selection. Once the region of interest is reached, the gradient may be varied so as to pass the region of interest through the constriction at a lower speed. The gradient may also be reversed to effect a reverse movement of the macromolecule through the restriction. This would be analogous to rewinding the cassette tape to a desired position. Accordingly, "play", "fast forward", "rewind", "pause" and "stop" functions can arise by controlling the magnitude and polarity of the gradient between the reservoirs.

Suitable signals that can be detected include a visual signal, an infrared signal, an ultraviolet signal, a radioactive signal, a magnetic signal, an electrical signal, an electromagnetic signal, or any combination thereof. Electrical signals are considered preferable for the reason that they are easily monitored, but other signals may be effectively monitored.

The macromolecule may include one or more labels; suitable labels include electron spin resonance molecule, a fluorescent molecule, a chemiluminescent molecule, an isotope, a radioisotope, an enzyme substrate, a biotin molecule, an avidin molecule, an electrical charge-transferring molecule, a semiconductor nanocrystal, a semiconductor nanoparticle, a colloid gold nanocrystal, a ligand, a microbead, a magnetic bead, a paramagnetic particle, a quantum dot, a chromogenic substrate, an affinity molecule, a protein, a peptide, a nucleic acid, a carbohydrate, an antigen, a hapten, an antibody, an antibody fragment, a lipid, a polymer, an electrically charged particle, a modified nucleotide, a chemical functional group, a chemical moiety, or any combination thereof. In some embodiments, the label is a chemical moiety such as a methyl group. This is shown in non-limiting fashion at FIG. 3b, which depicts a DNA strand labeled with several methyl groups and the detection of those methyl groups as indicative of the presence of one or more particular features of the labeled DNA.

Signals are, in some embodiments, inherently emitted by the macromolecule. Such inherently emitted signals include magnetic signals or radioactive signals, where the macromolecule or portions of the macromolecule are magnetic or radioactive. Where the signal is inherently emitted by the macromolecule, it may not also be necessary to illuminate the macromolecule so as to elicit a detectable signal.

In other embodiments, the signal is generated by illuminating the molecule. Illumination includes exposing at least a portion of the macromolecule to visible light, ultraviolet light, infrared light, x-rays, gamma rays, electromagnetic radiation, radio waves, radioactive particles, or any combination thereof. Suitable illumination devices include coherent and incoherent sources of light which can illuminate, excite, or even scatter from the macromolecule. UV, VIS, IR light sources can be used, such as lasers and other light surfaces.

Features of macromolecules detected by the disclosed methods include the size of the macromolecule, the molecular composition of the macromolecule, the molecular sequence of the macromolecule, an electrical property of one or more molecules of the macromolecule, a chemical property of one or more molecules of the macromolecule, a radioactive property of one or more molecules of the macromolecule, a magnetic property of one or more molecules of the macromolecule, or any combination thereof.

As discussed elsewhere herein, macromolecules are, in some embodiments, labeled. Accordingly, a feature of such macromolecule is the location of one or more labels of the macromolecule.

The molecular composition of a molecule is also characterized by the instant methods. The molecular composition includes the position of one or more molecules of the macromolecule, DNA polymorphisms, DNA copy number polymorphisms, amplifications within DNA, deletions within DNA, translocations within DNA, inversions of particular loci within DNA, the location of a methyl group within the macromolecule, or any combination thereof. Polymorphisms are, in some embodiments, detected by observing the presence of a labeled probe that is complementary only to that polymorphism.

The detection of binding sites between a drug and the macromolecule, macromolecule-drug complexes, DNA repairing sites, DNA binding sites, DNA cleaving sites, SiRNA binding sites, anti-sense binding sites, transcription factor binding sites, regulatory factor binding sites, restriction enzyme binding sites, restriction enzyme cleaving sites, or any combination thereof are all included within the present invention.

As discussed elsewhere herein, such features are determined by interrogating the macromolecule for the presence of one or more probes complementary to the features of interest. The methods are shown schematically in FIGS. 1c 2c, and 3c, each of which depicts the monitoring of a signal arising in connection with the passage of the macromolecule through the nanochannel constriction. In some embodiments, two or more probes are used to determine two or more features of a given macromolecule.

Certain embodiments of the device include a plurality of nanochannels. Such arrays of nanochannels are useful in efficiently characterizing multiple features of a single macromolecule or multiple features of multiple macromolecules. It will be apparent to one having ordinary skill in the art that labels complementary to certain features can be chosen and then applied to a given macromolecule that is then characterized to determine whether such features are present on that given macromolecule.

Also disclosed are devices for analyzing a linearized macromolecule. Suitable devices include two or more fluid reservoirs and a nanochannel comprising a constriction and the nanochannel placing the at least two fluid reservoirs in fluid communication with one another. As described elsewhere herein, suitable nanochannels are capable of physically constraining at least a portion of macromolecule so as to maintain that portion in linear form. This is set forth in further detail in U.S. Application No. 60/831,772, filed Jul. 19, 2006; U.S. Application No. 60/908,582, filed on Mar. 28, 2007, and U.S. Application No. 60/908,584, filed Mar. 28, 2007, the entirety of each of the aforementioned patent applications is incorporated by reference herein. Suitable devices with reservoirs can be made using standard silicon photolithographic and etching techniques. Nanochannel length can also be controlled using such techniques. Reservoirs and associated microfluidic regions, including the microfluidic interfacing regions, can be sealed using a standard wafer (Si wafer-Si wafer) bonding techniques, such as thermal bonding, adhesive bonding of a transparent lid (e.g., quartz, glass, or plastic).

The constriction suitably resides at one end of the nanochannel. In some embodiments, however, the constriction resides within the nanochannel. The ultimate location of the constriction will depend on the user's needs. Constrictions inside a nanochannel can be made as follows: using a sacrificial material as a filler as described further herein (see, e.g., Example 7 discussed further below).

Suitable nanochannels have a length in the range of at least about 10 nm, or at least about 15 nm, or at least about 20 nm, at least about 30 nm, at least about 50 nm, or even at least about 100 nm, at least about 500 nm, or at least about 1000 nm. In some embodiments, the nanochannel comprises a length at least equal to about the length of the linearized macromolecule.

Suitable nanochannels also have an effective inner diameter in the range of from about 0.5 nm to about 1000 nm, or in the range of from about 10 nm to about 500 nm, or in the range of from about 100 nm to about 300 nm, or in the range of from about 150 nm to about 250 nm. Nanochannel effective inner diameters can also be at least about 15 nm, or at least about 20 nm, or at least about 30 nm, or at least about 40 nm, or at least about 50 nm, or at least about 60 nm, or at least about 70 nm, or at least about 80 nm, or at least about 90 nm, or at least about 100 nm. As discussed, the nanochannel comprises an effective inner diameter capable of maintaining the macromolecule in linearized form.

The terms "effective inner diameter" and "inner diameter" are used interchangeably unless indicated otherwise. The term "effective inner diameter" refers not only to nanochannels having a circular cross-sectional area, but also to nanochannels having non-circularly shaped cross sectional areas. For example, the "effective inner diameter" can be determined by assuming the nanochannel has a circular cross section, and forcing the actual cross sectional area of the nanochannel to be effectively calculated in terms of the area of a circle having an effective inner diameter: Cross Sectional Area of Nanochannel=pi×(effective inner diameter/2)$^2$. Accordingly, the effective inner diameter of a nanochannel can be determined as:

$$\text{Effective Inner Diameter} = 2[(\text{Cross Sectional Area of Nanochannel})/\text{pi}]^{1/2}$$

Constrictions suitably have an effective inner diameter or effective dimension permitting molecular transport in the range of from about 0.5 nm to about 100 nm; or in the range of from about 1 to about 80 nm, or in the range of from about 5 to about 50 nm, or in the range of from about 8 nm to about 30 nm, or in the range of from about 10 nm to about 15 nm. Suitable constrictions have an effective inner diameter capable of maintaining a linearized macromolecule passing across the constriction in linearized form. The effective inner diameter or dimension can be controlled by controlling the etching conditions, or by controlling the size of the sacrificial material within the constriction region.

The disclosed devices also include a gradient, such gradients suitably existing along at least a portion of the nanochannel. Suitable gradients include an electroosmotic field, an electrophoretic field, capillary flow, a magnetic field, an electric field, a radioactive field, a mechanical force, an electroosmotic force, an electrophoretic force, an electrokinetic force, a temperature gradient, a pressure gradient, a surface property gradient, a capillary flow, or any combination thereof.

In some embodiments, the gradient is capable of linearizing at least a portion of a macromolecule residing within at least a portion of the nanochannel. In preferred embodiments, however, the gradient is capable of transporting at least a portion of a macromolecule located within the nanochannel along at least a portion of the nanochannel.

The devices suitably include a gradient generator capable of supplying the described gradient. Suitable generators include a voltage source, a magnet, an acoustic source, a pressure source, or any combination thereof.

The gradient generator is suitably capable of applying a constant gradient. The gradient generator is also, in some embodiments, capable of applying a variable gradient. The examples set forth elsewhere herein provide additional detail. It will be apparent to one having ordinary skill in the art that the intensity and variability of the gradient will be chosen according to the user's needs.

The two or more fluid reservoirs of the device comprise the same fluid in some embodiments. In other embodiments, the two or more fluid reservoirs comprise different fluids. In some embodiments, the different fluids may be used to themselves provide the gradient used to transport the macromolecule within the nanochannel—fluids of differing ionic strength or other property may be chosen to provide such a gradient. Suitable fluids include buffers, acids, bases, electrolytes, cell media, surfactants, and the like.

The devices also include a detector capable of detecting a signal arising from at least a portion of the linearized macromolecule passing through the constriction. Suitable detectors include a charge coupled device (CCD) detection system, a complementary metal-oxide semiconductor (CMOS) detection system, a photodiode detection system, a photo-multiplying tube detection system, a scintillation detection system, a photon counting detection system, an electron spin resonance detection system, a fluorescent detection system, a photon detection system, an electrical detection system, a photographic film detection system, a chemiluminescent detection system, an enzyme detection system, an atomic force microscopy (AFM) detection system, a scanning tunneling microscopy (STM) detection system, a scanning electron microscopy (SEM) detection system, an optical detection system, a nuclear magnetic resonance (NMR) detection system, a near field detection system, a total internal reflection (TIRF) detection system, a patch clamp detection system, an electrical current detection system, an electrical amplification detection system, a resistance measurement system, a capacitive detection system, and the like.

Suitable detectors are capable of monitoring one or more locations within one or more of the fluid reservoirs, or, in other embodiments, are capable of monitoring a location within the nanochannel, or even a location proximate to an end of the nanochannel. It will be apparent to the user that employing one or more detectors capable of detecting different signals at different locations would enable characterization of multiple features of a given macromolecule.

In some embodiments, the devices include an illuminator. Illuminators suitable include a laser, a source of visible light, a source of radioactive particles, a magnet, a source of ultraviolet light, a source of infrared light, or any combination thereof. The illuminator is used, in some embodiments, to excite a portion of the macromolecule within the nanochannel. As a non-limiting example, a source of light of a certain wavelength is used to excite fluorescent labels residing at certain, specific locations on the macromolecule so as to elicit the presence of such labels.

The devices also suitably include a data processor. In some embodiments, the devices include a data recorder. Such processors are used to manipulate and correlate large data sets.

Figure 4:
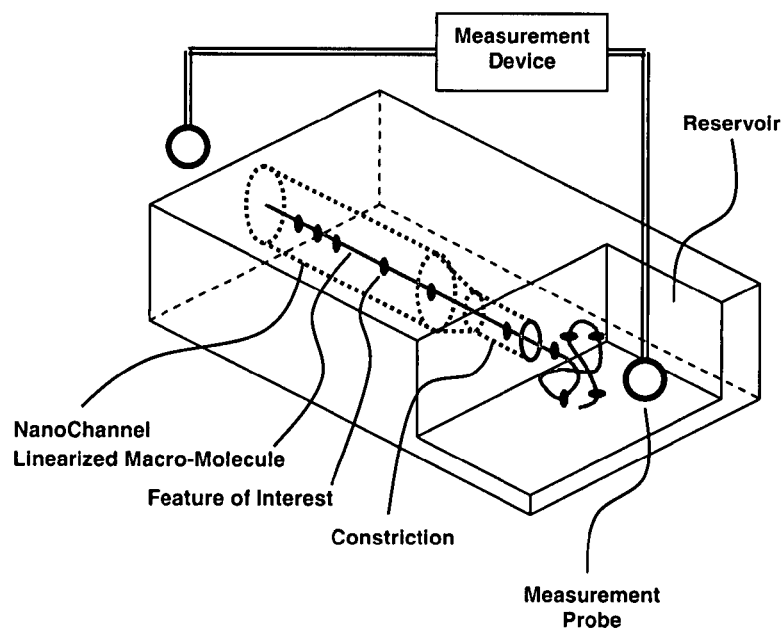
FIG. 4 depicts an representative embodiment of an enclosed nanochannel in communication with a reservoir, the nanochannel having a constriction of cross-sectional area smaller than remainder of nanochannel, and macromolecules being linearized within the nanochannel and features of interest on the molecule being detected as they pass through the constriction.
Figure 5:
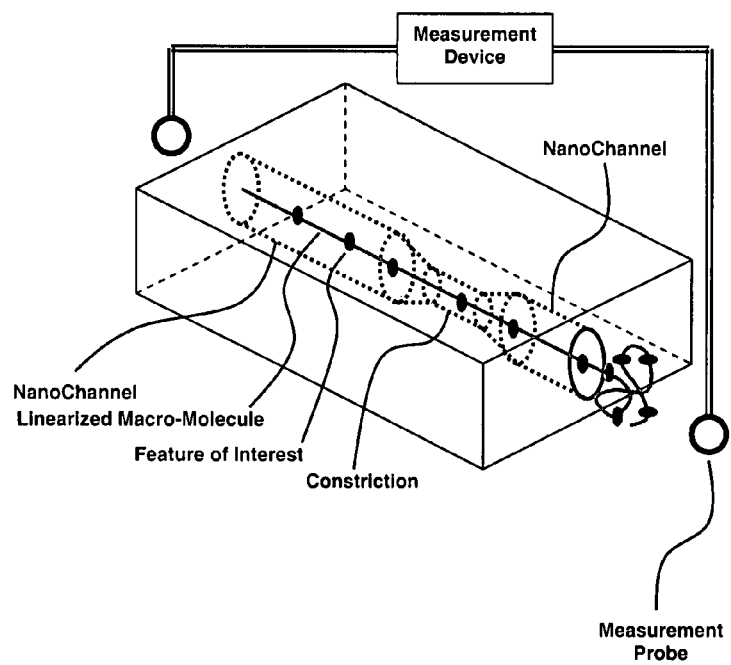
FIG. 5 depicts an enclosed nanochannel in communication with a second nanochannel via a constriction of cross-sectional area smaller than both nanochannels, macromolecules are linearized within the nanochannel and features of interest on the molecule are detected as they pass through the constriction.
Figure 6:
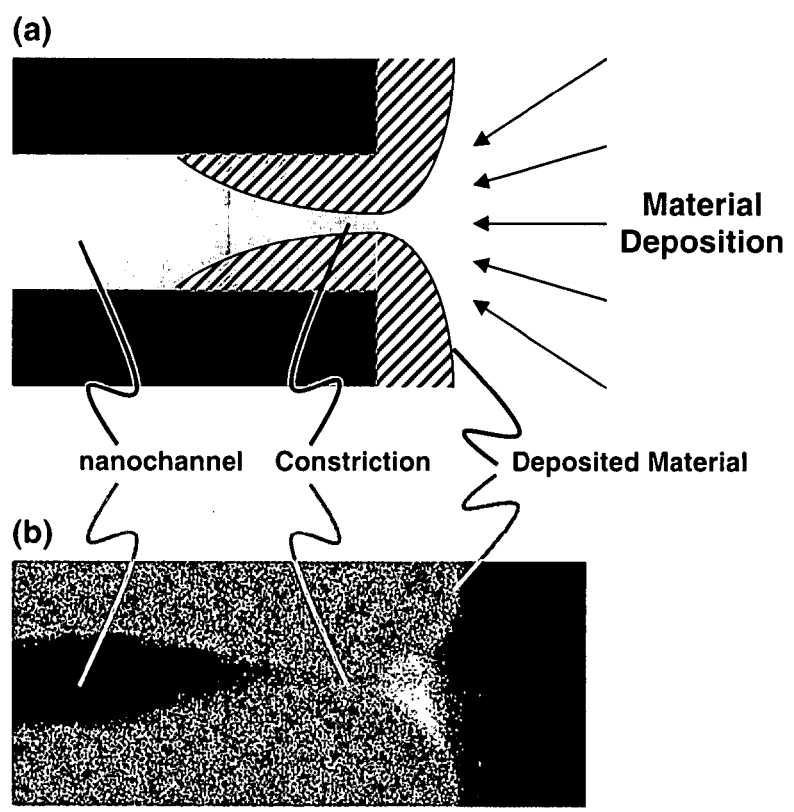
FIG. 6a depicts the preparation of a constriction at the end of a nanochannel by additive material deposition.
FIG. 6b is a scanning electron micrograph of an embodiment of such a constriction at the end of a nanochannel.
Figure 7:
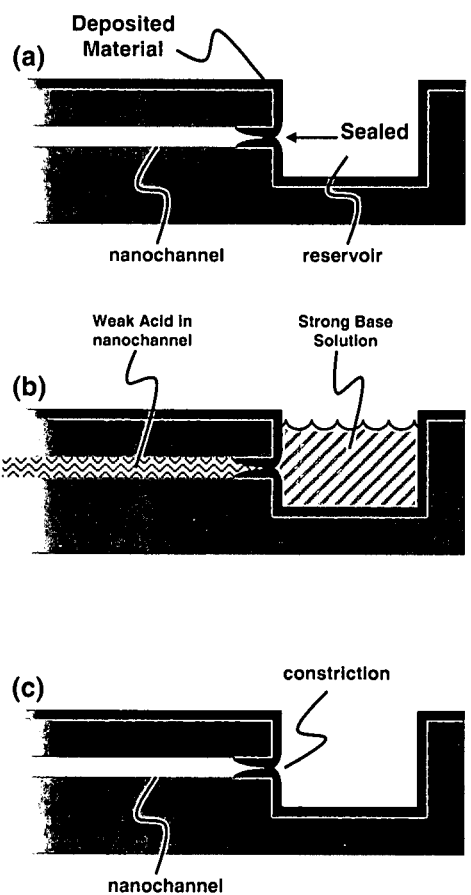
FIG. 7 depicts a representative fabrication of a constriction at the end of a nanochannel by (FIG. 7a) deposition of material at the end of the nanochannel resulting in complete sealing of the channel.
Figure 8:
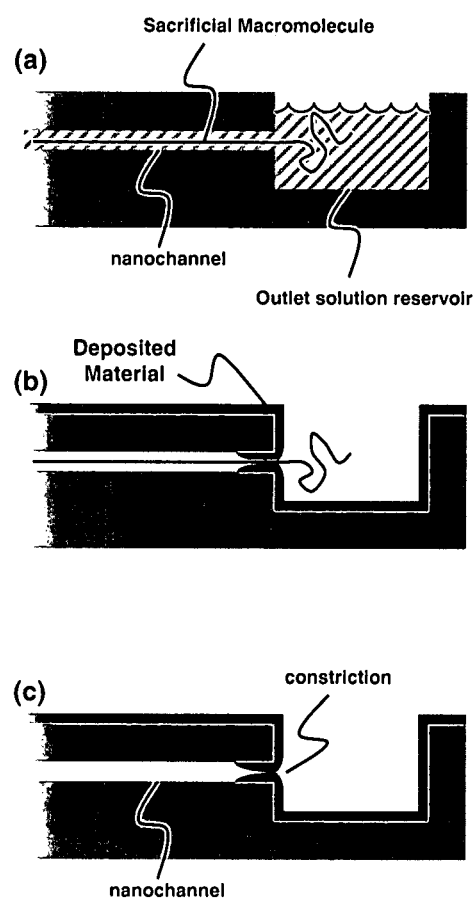
FIG. 8 depicts an representative fabrication of a constriction at the end of a nanochannel using sacrificial material.

One embodiment of the disclosed devices is shown in FIG. 4, which depicts a nanochannel constricted at one end proximate to a reservoir and a detector monitoring a signal arising out of a reservoir into which a macromolecule is linearly transported. Another embodiment is shown in FIG. 5, in which a constriction connects two nanochannels. In FIG. 5, it is seen that the detector monitors one or more signals evolved across the constricted nanochannel assembly.

As discussed elsewhere herein, where a comparatively long macromolecule is to be analyzed, one end of the macromolecule is first transported into one end of the nanochannel. As discussed, this may be accomplished by, for example, gradient structures, that assist such delivery; suitable gradient structures are described in U.S. Pat. No. 7,217,562, to Cao, et al., the entirety of which is incorporated by reference herein.

Also disclosed are methods for transporting a macromolecule. Such methods include providing at least two fluid reservoirs and providing an at least partially linearized macromolecule at least a portion of the macromolecule residing in a nanochannel. As discussed elsewhere herein, the macromolecule may be linearized by confinement in a suitably-dimensioned nanochannel having an inner diameter of less than about twice the radius of gyration of the linearized macromolecule.

Suitable nanochannels place the reservoirs in fluid communication with one another. Suitable nanochannels, as described elsewhere herein, also include a constriction. The dimensions of suitable constrictions are described elsewhere herein.

The methods also include the application of a gradient to the macromolecule. The gradient suitably gives rise to at least a portion of the linearized macromolecule being transported within at least a portion of the nanochannel. Suitable gradients include an electroosmotic field, an electrophoretic field, capillary flow, a magnetic field, an electric field, a radioactive field, a mechanical force, an electroosmotic force, an electrophoretic force, an electrokinetic force, a temperature gradient, a pressure gradient, a surface property gradient, a capillary flow, or any combination thereof. The gradient may suitably by constant or vary, depending on the needs of the user.

The reservoirs are generally larger in volume than that of the nanochannel segments. The reservoirs can be of almost any shape and size. For example, a reservoir may be circular, spherical, rectangular, or any combination thereof. The size of a reservoir will be dictated by the user's needs and may vary.

The nanochannels of the disclosed method have a length of greater than about 10 nm, or greater than about 12 nm, or greater than about 14 nm, or greater than about 16 nm, or greater than about 18 nm, or greater than about 20 nm, or greater than about 25 nm, or greater than about 30 nm, or greater than about 35 nm, or greater than about 40 nm, or greater than about 45 nm. In some embodiments, the nanochannels have a length of greater than about 100 nm or even greater than about 500 nm. Suitable nanochannels can also be greater than about 1 micron in length, or greater than about 10 microns, or greater than about 100 microns, or greater than about 1 mm, or even greater than about 10 mm in length. In some embodiments, the length of the nanochannel is chosen to exceed about the length of the linearized macromolecule.

Further disclosed are methods for fabricating constricted nanochannels. These methods first include providing a nanochannel. Suitable nanochannels have an effective internal diameter in the range of from about 0.5 nm to about 1000 nm, or in the range of from about 1 nm to about 500 nm, or in the range of from about 5 nm to about 100 nm, or in the range of from about 10 nm to about 15 nm. Nanochannel effective inner diameters can also be at least about 15 nm, or at least about 20 nm, or at least about 30 nm, or at least about 40 nm, or at least about 50 nm, or at least about 60 nm, or at least about 70 nm, or at least about 80 nm, or at least about 90 nm, or at least about 100 nm.

The methods also include the step of reducing the effective internal diameter of the nanochannel either at a location within the nanochannel, at a location proximate to the end of the nanochannel, or both, so as to give rise to a constriction within or adjacent to the nanochannel, the constriction having an internal diameter in fluidic communication with the nanochannel. Sample constrictions are shown in FIG. 1b, FIG. 4, FIG. 5, and FIG. 6. Suitable nanochannels are capable of maintaining a linearized macromolecule in its linearized form; as discussed elsewhere herein, this is suitably accomplished by using nanochannel segments of suitable dimensions so as to physically constrain the macromolecule to maintain the macromolecule in substantially linear form. The reduced internal diameter of the constricted nanochannel is suitably capable of permitting the passage of at least a portion of a linearized macromolecule.

Figure 9:
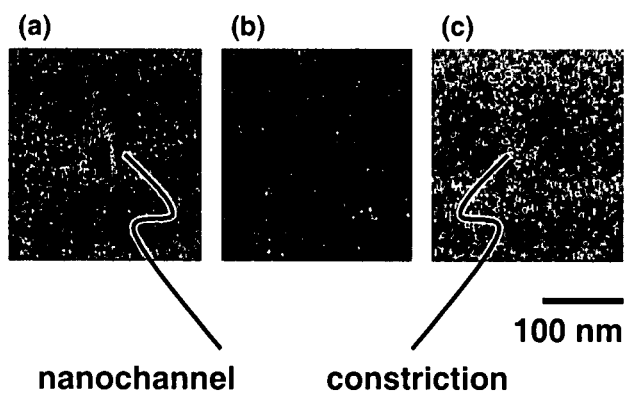
FIG. 9 presents a series of three scanning electron micrographs that describes the gradual reduction in size of a channel opening using additive deposition of material.

In one embodiment, the internal diameter of the nanochannel is reduced so as to form the constriction by additively depositing one or more materials within, or exterior to, the nanochannel. This is suitably accomplished by sputtering, spraying, physical vapor deposition, chemical vapor deposition, or any combination thereof. In some embodiments, the additive deposition ceases before the nanochannel is completely occluded. This is depicted in FIGS. 6a and 6b, where the deposition of additive material proximate to one end of a nanochannel is shown, the deposition ceasing before the nanochannel is completely occluded. Such a nanochannel is also shown in FIG. 9, in which the reduction in effective inner diameter is seen as the end of the nanochannel (FIG. 9a) is reduced by varied deposition (FIGS. 9b and 9c) of additive material.

In other embodiments of the invention, the additive deposition ceases after the nanochannel is completely occluded. In these embodiments, the methods include the step of re-opening the sealed nanochannel by removing at least a portion of the deposited additive material. This is suitably accomplished by etching. The etching process entails contacting one side of deposited additive material with an first species capable of etching the deposited additive material and contacting the other side of the deposited additive material with a second species capable of retarding the etching activity of the etch species upon contact with the first species. In some embodiments, the second species is capable of halting the etching activity of the etch species upon contact with the first species. This is depicted in FIG. 7a, where sealing material is applied at one end of a nanochannel and then, FIG. 7b, etched away by a strongly basic solution, the etching ceasing, FIG. 7c, when the basic solution etches through the sealing material and is neutralized by the strong acid residing on the opposite side of the sealing material. As will be apparent to those having ordinary skill in the art, the conditions in the nanochannel, the relative amounts of the first and second species, and other operating parameters will be adjusted so as to achieve the desired diameter.

In still other embodiments, reducing the internal diameter of the nanochannel includes several steps: (FIG. 8a) placing a sacrificial material within the nanochannel, (FIG. 8b) depositing additive material proximate to the sacrificial material so as to fully occlude the nanochannel, and (FIG. 8c) selectively removing at least a portion of the sacrificial material while leaving essentially intact the proximate additive material so as to give rise to a reduced internal diameter of the nanochannel of the dimension of the removed sacrificial material. It will be apparent to those having ordinary skill in the art that this aspect of the present invention is useful for fabricating voids having a variety of dimensions within nanoscale and larger channels or within other structures. DNA and carbon nanotubes are both considered suitable sacrificial materials. Other materials that may be selectively dissolved or etched away will be apparent to those having ordinary skill in the art.

The present invention also provides methods for linearizing macromolecules so as to constrain the degrees of freedom of the macromolecules from three dimensions to essentially one dimension. These methods include placing a macromolecule in a nanochannel, at least a portion of the nanochannel being capable of physically constraining at least a portion of the macromolecule so as to maintain in linear form that portion of the macromolecule.

The nanochannels suitably include a constriction. Suitable dimensions for constrictions are described elsewhere herein.

The methods also include, in some embodiments, applying a gradient to the macromolecule, such that at least a portion of the macromolecule passes, linearly, through the nanochannel constriction. Suitable gradients include an electroosmotic field, an electrophoretic field, capillary flow, a magnetic field, an electric field, a radioactive field, a mechanical force, an electroosmotic force, an electrophoretic force, an electrokinetic force, a temperature gradient, a pressure gradient, a surface property gradient, a capillary flow, or any combination thereof.

The microchannels of the disclosed methods suitable place two or more fluid reservoirs in fluid communication with one another.

The nanochannels suitable include an internal diameter of less than about two times the radius of gyration of the linear conformation of the macromolecule. Nanochannels suitably have lengths of at least about 10 nm, of at least about 50 nm, of at least about 100 nm, of at least about 500 nm. Suitable inner diameters for nanochannels are in the range of from about 0.5 nm to about 1000 nm, or in the range of from about 5 nm to about 200 nm, or in the range of from about 50 nm to about 100 nm.

EXAMPLES AND OTHER ILLUSTRATIVE EMBODIMENTS

The following are non-limiting examples and illustrative embodiments, and do not necessarily restrict the scope of the invention.

General Procedures.

Deposition of filling material was provided by sputtering, CVD, e-beam evaporation with a tilted sample wafer at various angles. This step was used to both reduce the nanochannel openings and create a tapered nozzle at the end of the channels.

Typically, to fabricate enclosed nanochannels, 100-340 nm of $SiO_2$ was deposited onto the channel openings. Effective sealing was achieved with various deposition conditions that were tested. At gas pressure of 30 mTorr, RF power of ~900 W, and DC bias of 1400 V, a deposition rate of ~9 nm/min was achieved. At lower pressure of 5 mTorr, the deposition rate was increased to an estimated 17 nm/min. Filling material was deposited on the nanochannel opening by sputtering at 5 mTorr. Further details about making nanochannel arrays and devices can be found in U.S. Patent Application Pub. Nos. US 2004-0033515 A1 and US 2004-0197843 A1, the entirety of which is incorporated by reference herein.

Example 1

A silicon substrate was provided having a plurality of parallel linear channels having a 150 nm trench width and a 150 nm trench height. These channel openings are sputtered at a gas pressure of 5 mTorr according to the general procedures given above. The sputter deposition time was 10-25 minutes to provide a nanochannel array that can either be partially sealed or completely sealed.

Example 2

This Example provides an enclosed nanochannel array using an e-beam deposition technique. A substrate can be provided as in Example 1. Silicon dioxide can be deposited by an e-beam (thermo) evaporator (Temescal BJD-1800) onto the substrate. The substrate can be placed at various angles incident to the depositing beam from the silicon dioxide source target; the deposition rate can be set to about 3 nm/minute and 150 nm of sealing material can be deposited in about 50 minutes. The angle of the incident depositing beam of sealing material can be varied to reduce the channel width and height to less than 150 nm and 150 nm, respectively, and to substantially seal the channels by providing shallow tangential deposition angles.

Example 3

In this example, a nanochannel array can be contacted with a surface-modifying agent. A nanochannel array made according to Example 1 can be submerged in solution to facilitate wetting and reduce non-specific binding. The solution can contain polyethylene glycol silane in toluene at concentrations ranging from 0.1-100 mM and remains in contact with the nanochannel array from about 1 hour to about 24 hours. Subsequent washing in ethanol and water is used to remove ungrafted material.

Example 4

This Example describes a sample reservoir with a nanochannel array for a nanofluidic chip. A nanochannel array having 100 nm wide, 100 nm deep nanochannels was made according to general procedures of Example 1. The nanochannel array was spin-coated with a photoresist such as AZ-5214E and patterned by photolithography with a photomask using a Karl Suss MA6 Aligner to provide regions on opposite ends of the channel array for preparing the reservoirs. The exposed areas were etched using reactive ion etching in a Plasma-Therm 720SLR using a combination of $CF_4$ and $O_2$ at a pressure of 5 mTorr and RF power of 100 W with an etch rate of 20 nm/min to expose the nanochannel ends and to provide a micron-deep reservoir about a millimeter wide on the opposite ends of the channels at the edge of the substrate.

Example 5

This Example describes filling a nanofluidic chip with a fluid containing DNA macromolecules to analyze DNA. A cylindrical-shaped plastic sample-delivery tube of 2 mm diameter was placed in fluid communication with one of the reservoirs of the nanochannel array of Example 3. The delivery tube can be connected to an external sample delivery/collection device, which can be in turn connected to a pressure/vacuum generating apparatus. The nanochannels are wetted using capillary action with a buffer solution. A buffer solution containing stained for example lambda phage macromolecules (lambda DNA) were introduced into the nanochannel array by electric field (at 1-50 V/cm); the solution concentration was 0.05-5 microgram/mL and the lambda DNA was stained at a ratio of 10:1 base pair/dye with TOTO-1 dye (Molecular Probes, Eugene, Oreg.). This solution of stained DNA was diluted to 0.01-0.05 microgram/mL into 0.5×TBE (tris-boroacetate buffer at pH 7.0) containing 0.1M of an anti-oxidant and 0.1% of a linear polyacrylamide used as an anti-sticking agent.

Example 6

This Example describes the fabrication of a nanozzle at end of nanochannel using acid etching. Fabrication of the nanozzle device begins with a completed silicon nanochannel having enclosed nanochannels as provided in Example 1. Creation of the nanopore proceeds by sputter coating a thin layer of chromium over the exposed end of the channel. Sputter coating using a Temescal system can be controlled with sub-nm precision with deposition amounts of 5-200 nm at a rate of 0.01-1 nm/sec or until the end of the nanochannel is completely covered with chromium. A wet-etch process can then be employed to open a sub-10 nm pore in the chromium. A dilute chromium etchant such as $Cr^{-7}$ can be flowed into the channel using capillary forces or other forms of pumping. Dilution can range from 1× to 10,000×. Because $Cr^{-7}$ is a highly selective acid etchant, it will preferentially react with the chromium at the end of the channel rather than the silicon channels themselves. To stop the etch once a pore has opened, the area outside the channel will be filled with a highly concentrated base solution (such as sodium hydroxide) that will rapidly neutralize the weak acid upon breakthrough. After subsequent washing of the device, the result will be a nanoscale nozzle at the end of a nanochannel.

Example 7

This Example describes how to fabricate a nanonozzle chip using a sacrificial macromolecule. A nanofluidic chip with input/output fluid reservoirs connected by nanochannels is used to linearize double strand DNA (FIG. 8a). In this example, long fragments of DNA, approximately 1-10 Mbp in length, uniformly stained with YOYO-1 is preferable. The concentration of the DNA should be around 0.5 micrograms/mL, with the dye stained to a ratio of 10:1 base pair/dye. The buffer solution is composed of 0.5×TBE (tris-boroacetate buffer at pH 7.0) containing 0.1M of an anti-oxidant and 0.1% of a linear polyacrylamide used as an anti-sticking agent. Using the nanofluidic chip and procedure described previously (Cao 2002), the solution of sacrificial DNA molecules are flowed into the nanochannels of the chip, where they exit the nanochannels at the outlet reservoir. Using a fluorescent imaging microscope, the exit of the DNA molecules is observed in real time, and their movement controlled by applying an electric field across the reservoirs (1-50 V/cm). With such a scheme, a desired DNA fragment's position can be suspended having only partially exited the nanochannel. The nanochannel chip is then dried at 50° C. in vacuum environment removing any residual buffer solution, so that the DNA fragment of interest remains partially inside the nanochannel. Interaction between the nanochannel surface and the DNA fragment, such as through van der Waals bonding, maintains the fragment's position in the channel during the drying process.

After the nanochannel chip has been dried, a material such as silicon dioxide is deposited over the surface of the chip (FIG. 8b) such that the entrance to the nanochannel becomes blocked, and the DNA fragment enclosed. The rate of material deposition and the temperature of the deposition must be carefully chosen such that the DNA fragment is not damaged during this process. Evaporating material at 0.2 A/s or less on a sample kept at −160° C. using a cooling stage has been shown to protect small organic molecules from damage (Austin 2003). In order to obtain uniform coverage around the nanochannel to properly form a nanonozzle, the stage is rotated and tilted during the evaporation process. To completely close a nanochannel of 80 nm in diameter, approximately 200 nm of silicon dioxide material should be evaporated.

Example 8

Operation of a Device

Electrical Measurement for Sequencing Single-Stranded Nucleic Acid

A voltage bias is applied across a nanochannel device having a constriction (either nanogate or nanozzle) approximately 1.5 nm inner diameter placed at one end of the nanochannel, the nanochannel being about 200 microns in length, for a single strand nucleic acid for sequencing using electrodes (can be copper, silver, titanium, platinum, gold, or aluminum) contacting reservoirs at each end of the nanochannel, the reservoirs having dimensions of about 5-100 microns in diameter and 1-2 microns deep. The electrodes are deposited into the reservoirs and lead lines leading to outside the fluidic region for connection to a current monitor. A voltage range of 100 mV-100V can be used. Biological buffer (TE, TBE, TAE) is placed in each reservoir, capillary action and a pressure differential aids in wetting the nanofluidic device using a suitable fluidic delivery pump or syringe. A nucleic acid sample (e.g., 100 base sDNA and up, at least 1000 bases, or 10000 bases, or 100000 bases, or 1 million, or even 10 million, or even 100 million, up to chromosomal length) in buffer solution (1 nanoliter up to about 100 microliters) is delivered to one or both of the reservoirs. A gradient is applied to aid in the transport of one or more polynucleic acid molecules into the nanochannel in into the constriction. A field is applied, specifically in this example, a controlled voltage gradient to apply a current from one reservoir, through the nanochannel, through the constriction with the polynucleic acid residing within the constriction, and into the second reservoir. The electrical current flowing through this system is detected and amplified using an Axopatch 200B (Molecular Devices) patch clamp amplifier. Typical measured currents range from about 100 fA to about 1 uA with fluctuations approximately hundreds of picoamps as the DNA moves through the constriction. Labels attached to the single strand DNA can produce additional current fluctuations of magnitude smaller than that created by the DNA itself. For the case of measurements with a spatial resolution of a single base, typical translocation speed is such that the measurement system can register a minimum of 1 measurement per base. In the case of the Axopatch 200B with 100 kHz bandwidth, the maximum translocation speed is 100 kB/sec, assuming 50% stretching of the DNA molecule in the nanochannel. This gives rise to a translocation speed of the DNA through the construction to be about 0.015 nm/microsec. The measure current differences are measured and correlated to a set of calibration standards to give rise to the sequence of the DNA sample.

A sample table tabulating suitable cross-sectional dimensions for the analysis of various target molecules is shown below:

TABLE

| Target Molecule Analyzed | Minimum cross-sectional dimension of Constriction (nm) |
| --- | --- |
| ss-DNA | 1.5 |
| ss-DNA + complementary strands | 2 |
| ds-DNA with nick, gap or lesion | 2 |
| ds-DNA | 2 |
| ds-DNA + moiety (eg. Methyl group, labeling group) | 2.1 |
| ds-DNA + small compound | 2.5 |
| ds-DNA + 3rd strand probe | 3.5 |
| ds-DNA + biotin | 5 |
| ds-DNA + protein bound factors (eg. Transcription factors) | 4-15 |
| ds-DNA + bead (eg. Quantum dot, magnetic beads) | 10-50 |

What is claimed:

1. A device for analyzing a polynucleotide macromolecule, comprising:
   two or more fluid reservoirs joined by a fluid pathway;
   a nanochannel having an effective inner diameter between about 10 nm and about 500 nm;
   a discrete constriction in or at a terminal end of the nanochannel, having an effective inner diameter that is no more than about 40% of the effective inner diameter of the nanochannel, wherein the nanochannel and the constriction are located in the fluid pathway between the reservoirs, wherein the constriction is capable of maintaining a linearized polynucleotide macromolecule passing across the constriction in a linearized form, wherein the constriction is configured to locally reduce the effective inner diameter of the nanochannel to be about 0.5 nm to about 100 nm; and
   a sensor associated with the device located to detect a signal from at least a portion of the polynucleotide macromolecule as it passes through the constriction.

2. The device of claim 1, wherein the constriction resides at one end of the nanochannel.

3. The device of claim 1, wherein the constriction resides within the nanochannel.

4. The device of claim 1, wherein the nanochannel comprises a length in the range of at least about 50 nm.

5. The device of claim 1, wherein the nanochannel comprises a length in the range of at least about 100 nm.

6. The device of claim 1, wherein the nanochannel comprises a length in the range of at least about 500 nm.

7. The device of claim 1, wherein the nanochannel comprises a length at least equal to the length of the linearized macromolecule.

8. The device of claim 1, wherein the nanochannel comprises an effective inner diameter in the range of from about 100 nm to about 300 nm.

9. The device of claim 1, wherein the nanochannel comprises an effective inner diameter in the range of from about 150 nm to about 250 nm.

10. The device of claim 1, wherein the constriction comprises an effective inner diameter in the range of from about 10 to about 50 nm.

11. The device of claim 1, wherein the constriction comprises an effective inner diameter capable of maintaining the linearized polynucleotide macromolecule passing across the constriction in linearized form.

12. The device of claim 1, wherein the device further comprises a gradient.

13. The device of claim 12, wherein the gradient is selected from the group consisting of: an electroosmotic field, an electrophoretic field, a magnetic field, an electric field, a radioactive field, a mechanical force, an electroosmotic force, an electrophoretic force, an electrokinetic force, a temperature gradient, a pressure gradient, a surface property gradient, a capillary flow, and any combination thereof.

14. The device of claim 12, wherein the gradient is capable of linearizing at least a portion of the polynucleotide macromolecule residing within at least a portion of the nanochannel.

15. The device of claim 12, wherein the gradient is capable of transporting at least a portion of the polynucleotide macromolecule located within the nanochannel along at least a portion of the nanochannel.

16. The device of claim 12, further comprising a gradient generator.

17. The device of claim 16, wherein the gradient generator is selected from the group consisting of: a voltage source, a magnet, an acoustic source, a pressure source, and any combination thereof.

18. The device of claim 12, wherein the gradient generator is capable of applying a constant gradient.

19. The device of claim 12, wherein the gradient generator is capable of applying a variable gradient.

20. The device of claim 1, wherein the two or more fluid reservoirs comprise the same fluid.

21. The device of claim 1, wherein the two or more fluid reservoirs comprise different fluids.

22. The device of claim 1, wherein the sensor is selected from the group consisting of: a charge coupled device (CCD) detection system, a complementary metal-oxide semiconductor (CMOS) detection system, a photo diode detection system, a photo-multiplying tube detection system, a scintillation detection system, a photon counting detection system, an electron spin resonance detection system, a fluorescent detection system, a photon detection system, an electrical detection system, a photographic film detection system, a chemiluminescent detection system, an enzyme detection system, an atomic force microscopy (AFM) detection system, a scanning tunneling microscopy (STM) detection system, a scanning electron microscopy (SEM) detection system, an optical detection system, a nuclear magnetic resonance (NMR) detection system, a near field detection system, a total internal reflection (TIRF) detection system, a patch clamp detection system, an electrical current detection system, an electrical amplification detection system, a resistance measurement system, a capacitive detection system, and any combination thereof.

23. The device of claim 22, wherein the sensor is capable of monitoring one or more locations within one or more of the fluid reservoirs.

24. The device of claim 22, wherein the sensor is capable of monitoring a location within the nanochannel.

25. The device of claim 22, wherein the sensor is capable of monitoring a location proximate to an end of the nanochannel.

26. The device of claim 1, further comprising an illuminator.

27. The device of claim 26, wherein the illuminator is selected from the group consisting of: a laser, a source of visible light, a magnet, a source of ultraviolet light, a source of infrared light, and any combination thereof.

28. The device of claim 1, further comprising a data processor.

29. The device of claim 1, wherein the constriction is disposed within the nanochannel proximate to a terminus of the nanochannel.

30. The device of claim 1, wherein the constriction is configured to locally reduce the effective inner diameter of the nanochannel to be about 1.5 nm to about 10 nm.

31. The device of claim 1, wherein the nanochannel has a length that is at least 1000 nm.

* * * * *

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 1
aagtgatttg gcgaatccaa gggacgttac          30

<210> SEQ ID NO 2
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 2
gtaacgtccc ttggattcgc caaatcactt          30

<210> SEQ ID NO 3
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 3
aacgcgggcg ataacgcgct accgtcgcgt          30

<210> SEQ ID NO 4
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 4
acgcgacggt agcgcgttat cgcccgcgtt          30